United States Patent [19]

Hachiya et al.

[11] 4,446,130

[45] May 1, 1984

[54] METHOD OF PREPARING DRIED GINSENG FOR DRUG

[75] Inventors: Iwao Hachiya, Yokohama; Keizo Mochizuki, Kawasaki; Yukio Kuwada, Yokohama, all of Japan

[73] Assignee: Meiji Seika Kaisha, Ltd., Tokyo, Japan

[21] Appl. No.: 252,175

[22] Filed: Apr. 8, 1981

[30] Foreign Application Priority Data

Apr. 18, 1980 [JP] Japan .................................. 55-50361

[51] Int. Cl.$^3$ .............................................. A61K 35/78
[52] U.S. Cl. ................................................... 424/195
[58] Field of Search ................... 424/195; 219/10.55 E

[56] References Cited

U.S. PATENT DOCUMENTS

| | | | |
|---|---|---|---|
| 2,495,435 | 1/1950 | Welch | 219/10.55 E |
| 3,311,287 | 3/1967 | Long et al. | 219/10.55 E |
| 3,490,580 | 1/1970 | Brumfield et al. | 219/10.55 E |

OTHER PUBLICATIONS

Food Engineering, "Processing Issue", Nov. 1964, (4 pages) entitled Consider Microwaves.

Primary Examiner—Sam Rosen
Assistant Examiner—John W. Rollins
Attorney, Agent, or Firm—Francis A. Keegan

[57] ABSTRACT

A dried ginseng is obtained by heating a crude or raw ginseng to soften its tissue, freezing the softened ginseng in an inert gas under pressure and then lyophilizing the frozen ginseng under reduced pressure in a conventional way. This dried ginseng retains its original miscellaneous shape and color tone inherent to the crude ginseng, is ready for extraction of the pharmacologically active ingredients therefrom when dipped in aqueous ethanol for preparation of medicinal spirit beverage and can stand long storage without spoilage by bacterial and fungal infestation.

5 Claims, No Drawings

METHOD OF PREPARING DRIED GINSENG FOR DRUG

SUMMARY OF THE INVENTION

This invention relates to a method of preparing a dried ginseng for drug which retains its original miscellaneous figure or shape and color tone inherent to the untreated crude or raw ginseng, from which the pharmacologically active ingredients are readily extractable upon dipping in an aqueous ethanol and which can endure storage for a long time.

More particularly, this invention envisages to provide a dried ginseng which will restore to its original miscellaneous shape and color tone characteristic of the crude ginseng when dipped and stored in aqueous ethanol in a container or bottle, which can provide beverage or liquor drug or medicinal spirit beverage as the ethanolic extract solution or elixir obtained by dipping this in aqueous ethanol, and of which miscellaneous appearance or shape as regained by dipping in and storing in the aqueous ethanol in a transparent container may be appreciated or admired aesthetically

BACKGROUND OF THE INVENTION

The roots of ginseng plants, including Panax ginseng (also called *Panax schinseng*), *Panax pseudo-ginseng*, *Panax quinquefolium* and *Panax japonicum* contain saponins and sapogenins and have long been used as crude drugs. The roots of these ginseng plants and a dried product are called "ginseng drug" or merely "ginseng". In many countries of Asia, people have said that the ginseng is a very valuable medicine which promotes health and enhances man's lease of life. Recently it has scientifically been confirmed that ginseng exhibits some sedative activity, stimulative activity and diuretic activity. It has been reported that ginseng, namely the crude drugs which are obtained from the ginseng plants, contain inter alia saponins, sapogenins, vitamin B group compound, and β-sitosterol D-glucoside, as the active or medicinal ingredients but it has been elucidated that the main active ingredients of ginseng are saponins and sapogenins (see the specification of U.K. Pat. No. 1,348,324).

The root of ginseng plants has several branched small roots and a number of long, thin fibre-like roots and exhibits a unique and miscellaneous appearance and shape which are worthy of being appreciated or admired aesthetically. Besides, the raw root of the ginseng plants, that is the crude ginseng, is likely to be spoiled by bacterial and fungal infestation during storage and often is stored while being dipped in aqueous ethanol containing usually 40~80% water. This storage of ginseng in aqueous ethanol may be done in a transparent vessel made of, for example, glass cylinder containing a volume of aqueous ethanol for the purpose of aesthetic appreciation or admiration of the miscellaneous appearance or shape of the ginseng root.

In order to prevent the crude ginseng from spoiling, the crude ginseng is often dehydrated, affording dried ginseng. The dried ginseng is easy to be handled in the commercial route and may be dipped in aqueous ethanol to restore its original miscellaneous shape of the crude ginseng. When the dried ginseng is dipped in aqueous ethanol, the pharmacologically active ingredients of the ginseng can be extracted into the ethanol, and the ethanolic extract (the elixir) so obtained is useful as medicinal spirit beverage or liquor drug which maintains and promotes the health of men.

The dried ginsengs known heretofore include those which have been sun-dried and those which have been dried by hot air and sun-dried, and they are called Ginseng Radix alba or Ginseng Radix rubra. Ginseng Radix alba is the one obtained by peeling the outer skin off from the crude ginseng root (often called as Ginseng Radix) and then drying under sunlight, while Ginseng Radix rubra is produced by treating the crude Ginseng Radix as such with hot water or steam and then drying under sunlight or by hot air. Ginseng Radix is thus made from the root of ginseng plants belonging to the family Araliaceae, and the main part of this root consists of compact and rigid tissue cells, significantly different from those soft and flexible tissue cells of the usual cultivated vegetable carrot which belong to the family Umbelliferae. The outer skin of this ginseng root consists of phellem (cork-tissue) and collenchyma and its xylem has compact and rigid fibrous tissue, so that the aforementioned drying by sunlight or hot air applied to the ginseng root is usually not complete and substantially renders a high content of moisture to be remaining in the dried products of Panax Radix alba and rubra. This amount of residual water will tend to deteriorate the dried ginseng due to infestation with fungi and bacteria during the storage. Besides, the drying by sunlight or hoot air is likely to bring about shriveling and hardending of ginseng tissue in the course of drying, which, in turn, give rise to considerable deformation and discoloration of ginseng. When the dried ginseng as dehydrated in the above ways are dipped in aqueous ethanol for the purpose of aesthetical appreciation, therefore, they do not restore completely to the original miscellaneous shape and color tone characteristic of and inherent to the untreated crude ginseng and hence have far less value in the view-point of aesthetic appreciation. Further, it is difficult for the dipping aqueous ethanol to permeate into the dried ginseng due to their shrivelled and hardened tissue structure disadvantageously to the extent that it will take at least three months before the aqueous ethanol in which the dried ginseng has been dipped becomes suitable for liquor drug or medicinal beverage. Thus, the pharmacologically active ingredients in the ginseng can only be very slowly extracted into the aqueous ethanol from the previously known dried ginsengs.

Japanese Patent Publication No. 30567/77 describes a method for preparation of a dried ginseng according to the lyophilization (freeze-drying) technique. The prior method of this Japanese Patent comprises forming appropriate numbers of elongate apertures lengthwise within the main trunk of crude ginseng substantially along the central axis of said trunk root and then lyophilizing the pierced root in vacuum. The elongate apertures formed enable fairly rapid drying to proceed to the central part of the ginseng, and the dried ginseng so obtained rather retains the original shape and color tone of the crude ginseng than those of the usual dried products of Ginseng Radix alba and rubra as already noted. The above method according to the lyophilization technique has another advantage that ice crystals develop within the root tissue upon the freezing and can subsequently sublime during the lyophilization to leave many cavities or pores therein, which facilitate smooth permeation of the dipping aqueous ethanol into the dried ginseng and thus rapid extraction of the active ingredients therefrom, to make the ethanolic extract solution suitable for medicinal beverage soon, eg. in about one week.

According to the above method, however, the elongate apertures should be formed by inserting or piercing fine needles at proper places near the crotches of branched small roots extending from the trunk root, upwardly to the central part of the trunk root in such a manner that the aesthetically appreciable appearance of the ginseng product would not be damaged by exposure of the apertures as formed. Since one crude ginseng is extremely different in its shape from another, the proper sites in crude ginseng at which the needle-piercing is to be made vary from one to another. Thus, the work of needle-piercing is impossible to be done mechanically, and it is necessary to check visually and preliminarily decide the proper sites with every ginseng, before carrying out the piercing operation.

Therefore, the work of needle-piercing needs inefficient hand-operation. Moreover, while the dried ginseng obtained by the above-mentioned method has not changed greatly in the shape and color tone, it has been reduced greatly in the size to the degree that the main root trunk diameter is decreased by 17 to 38% as compared to the initial diameter of the raw root trunk. This is because inevitable shriveling took place during the drying step, with lengthwise extending deep wrinkles being formed in the root trunk portion. When the dried ginseng so obtained is dipped in aqueous ethanol, it does not regenerate completely the original shape of crude ginseng, and it looks worse and is far less worthy of being appreciated aesthetically than the orginal crude ginseng.

Further drawback of the method of the aforesaid Japanese Patent occurs due to that crude ginseng has such shape that several branched small roots and fibre-like thin roots are spreading in all directions from the main root trunk portion. Thus, the crude ginseng is too voluminous and hence disadvantageously it can only be frozen and lyophilized with poor efficiency requiring a higher cost for the drying.

We have closely studied these circumstances in an attempt to avoid the above-mentioned drawbacks encountered in the course of the freezing and lyophilization of crude ginseng. As a result, we have now found that a dried ginseng for drugs which fully retains the miscellaneous original shape and color tone inherent to crude ginseng, which permits easy extraction of the pharmacologically active ingredients from the dried product and which is highly worthy of aesthetic appreciation and stands the storage for a long time, can be prepared by a method comprising heating crude ginseng to soften its tissue structure, followed by freezing in an inert gas under pressure and then by lyophilization (freeze-drying).

SUMMARY OF THE INVENTION

According to this invention, there is provided a method of preparing a dried ginseng for drugs which comprises the sequential steps of placing a crude ginseng in a heat-resistant and heat-sealable bag or container, sealing the bag or container, heating the ginseng packed in the bag or container to a temperature in the range of from 60° C. to 100° C. until the tissue of the ginseng is softened, romoving the softened ginseng from the bag or container, freezing the ginseng in an inert gas under pressure in a pressure-resistant vessel, and finally lyophilizing the frozen ginseng under reduced pressure in a conventional way.

DETAILED DESCRIPTION OF THE INVENTION

According to the method of this invention, it is essential that a cleaned crude ginseng is heated to a temperature of from 60° C. to 100° C. to soften the tissue of the ginseng. The heating treatment is carried out while the ginseng is being placed in a sealed heat-resistant bag or container, in order to prevent dissipation of the pharmacologically active and flavor ingredients of the crude ginseng and also to prevent hardening of the ginseng tissue would otherwise occur due to partial drying of the root. If the temperature of the crude ginseng heated is lower than 60° C., the tissue of the ginseng will not be softened and besides the quality of the final dried ginseng will be deteriorated due to enhanced enzymatic action which proceeds in this heating step. The ginseng temperatures exceeding 100° C., on the other hand, will cause rapid gelatinization of the starch of the ginseng and cause the trunk root and branch roots to be broken by swelling pressure which arises from the starch gelatinization. As a consequence, some components of the ginseng, including starch will be exposed to the high temperature at the surfaces of the broken areas of roots, leading to damage of the shape and loss of the pharamacologically active ingredients. In addition, the too high temperature may bring about violent generation of water vapor from the interior of the ginseng roots, with the result of necessity to increase the mechanical strength of the bag or container to be used.

According to the known method of producing Ginseng Radix rubra, the crude ginseng is directly dipped in hot water or steamed without being packed in the bag or container, and then the flavor ingredients of the ginseng can dissipate into air and also into the hot water employed, with the pharmacologically active ingredients of the ginseng being lost by extraction into the hot water. Further, when the crude ginseng is heated with hot air without being packed in the bag or container, hardening and shriveling of the ginseng tissue can take place due to dissipation of the water content of the ginseng. Therefore, in the method of this invention, the crude ginseng is heated while being packed or placed within the sealed bag or container.

In a general embodiment of heating the crude ginseng which is placed in the sealed bag or container, the whole bag or container containing the crude ginseng therein may externally be heated by means of hot water, steam and/or microwaves (i.e. high-frequency electromagnetic waves) in such way that the crude ginseng is maintained at a temperature of 60° to 100° C. for a period of several minutes until the tissue of the ginseng is softened to a satisfactory extent, and thereafter the ginseng is allowed to cool to ambient temperature.

If a great amount of heat is applied at a time in the above heating step, the gelatinization of the starch in the cell tissue of the crude ginseng will take place, giving rise to the swelling pressure which breaks the trunk root and branch roots and damages the original miscellaneous shape of ginseng. It is thus necessary to control the intensity of heating, depending on the size and shape of the crude ginseng used. From this point of view, the most suitable heating means is to heat the packed ginseng by processing with microwaves which enables the ginseng to be uniformly heated throughout its interior. In a convenient way for microwave heating, crude ginseng is placed in a bag of a heat-resistant and microwave-permeable film material made of, for example, polyethylene, polyvinyl chloride, polyester or polycarbonate or in a heat-resistant, microwave-permeably container made of, for example glass; and the film bag or container is sealed followed by processing with microwaves. The heat-resistant film bag under discussion is advantageous in its handling since it is not damaged by heating during the softening treatment of the ginseng and readily sealable by the heat-sealing apparatus.

In an alternative way, crude ginseng may be introduced into a closable vessel provided with a microwave processing equipment, where the ginseng in said vessel may be heated by being processed with the microwaves for the softening step, after closing of the vessel. This alternative way requires the extra expensive equipment for the irradiation with microwave, so that it is less practical and advantageous than the embodiment where the film bag or glass container containing the ginseng therein is heated by means of a commercially available conventional microwave heating device.

The microwave heating may preferably be effected intermittently. Thus, the microwave processing is made to raise the temperature of the crude ginseng to the order of 60°~100° C. and then the ginseng is allowed to freely stand for 1 to 3 minutes without processing with microwaves, when the tissue of the ginseng is caused to be softened. Subsequently, the microwave processing and the free standing of ginseng for further softening without microwaves processing are alternately repeated twice or more appropriate times.

If a too great amount of heat is applied at a time to the crude ginseng, the rapid elevation of its temperature will take place too earlily before the ginseng tissue is softened as desired, whereupon the starch of the ginseng tissue can be gelatinized resulting in the breakage of the trunk root and branch roots due to the swelling pressure generated internally as discussed hereinabove.

In order to avoid these undesirable phenomenon, it is preferable to repeat alternately the operation of the microwave processing and the free standing of ginseng at the prevailing temperature. As a matter of course, external heating means, for example, with hot air, hot water, steam and the like may also be used instead of the microwave processing. However, when the crude ginseng placed in a sealed bag or container is heated externally with hot air, hot water or steam, the conduction of heat from the heating medium to the container is involved and hence not only delays the rise in temperature of the ginseng but causes a gap in temperature distribution between the exterior and the interior of the ginseng. In consequence, the external heating with hot air, hot water or steam is not so desirable for the purpose of uniformly softening the tissue of the ginseng in a short time, and it requires, depending upon the size of the crude ginseng to be softened, a relatively long time of from 15 to 60 minutes occasionally with accompanying a thermal degradation and loss of the effective ingredients in the crude ginseng. While, the microwave processing permits the crude ginseng to be readily and uniformly softened in a reduced time of totally about 5 minutes irrespectively of its size, during which the loss by water vapour extraction and thermal degradation of the effective ingredients of the ginseng do not occur to a appreciable degree.

The ginseng which has been softened in the above way generally indicates such hardness, as measured by a penetrometer (manufactured by Kiya Seisakujo K.K., Japan) provided with a penetrating cyrindrical rod of 5 mm diameter and made of stainless steel, that the lower, flat end of said rod will penetrate into the outer surface and inner tissue of the ginseng under a loading of from 2.5 to 12 kg. This loading is the minimum which is required to compel the penetrating rod to break through the outer surface and pierce into the inner tissue of the ginseng. This minimum loading as defined above is referred to herein as the hardness of the ginseng material under discussion. The untreated crude ginseng usually has a hardness of 23.5 kg. Thus, the crude ginseng has been softened to a degree of from half to one tenth of the original hardness by the heating treatment of the present method.

The softened ginseng is subsequently removed from the sealed bag, container or vessel after cooling to room temperature, and the branch roots and fibre-like roots extending in all directions from the trunk root of the ginseng are arranged to be put together coherently in the direction along the trunk root of ginseng so that the occupying space of the whole ginseng is reduced. The coherent arrangement of the roots of the ginseng in this way will appreciably improve the efficiency of the subsequent freezing and lyophilization steps. The coherent body of the ginseng is then charged into a pressure-resistant closed vessel, into which an inert gas, for instance, gaseous hydrocarbons such as methane, nitrogen or air is filled to an internal gas pressure of 20 kg/cm$^2$ or higher and generally up to about 70 kg/cm$^2$. In the pressurized vessel the ginseng is frozen at a low temperature, for example, of from $-10°$ to $-30°$ C., after which the vessel is degassed. Then the frozen ginseng is subjected to lyophilization under reduced pressure in a conventional way. There is thus obtained a dried ginseng which fully retains the original shape and color tone inherent to the crude ginseng, which is highly susceptible to the extraction of the pharmacologically active ingredients therefrom and which can stand the storage for a long time.

When the crude ginseng is not softened (that is, the softening step of crude ginseng is omitted) but the crude ginseng is directly frozen in the inert gas under pressure and then lyophilized under reduced pressure in a usual way, the drying rate of the frozen crude ginseng upon the lyophylization step is higher and the shriveling of the trunk root occurs only to a lesser degree during the drying as compared to such a case where the crude ginseng is directly frozen under atmospheric pressure and then lyophilized under reduced pressure in a usual way. In the former case, however, the pronounced drawbacks will be found that the residual amount of the high-pressure gas remaining in the ginseng tissue will burst the tissue in the lyophilization step, to induce deep cracks in the trunk root and branch roots and sometimes more unfavorably to form deep split in the tissue reaching to the core of the ginseng body. The dried ginseng so obtained will be evaluated as defective or reject and is far away from being worthy of appreciation.

The method of this invention includes the softening step of the ginseng tissue previously accomplished and thereby can perfectly prevent the formation of cracks which would otherwise occur during the lyophilization step. This effect achieved by the softening is of great significance. The reason why the above-mentioned noticeable effect of preventing the cracks or splits can be obtained by the softening treatment of the present method is not fully elucidated but is assumedly attributable to that the softening treatment would modify the tissue structure of the crude ginseng into a gas-permeable one and would allow rapid release, upon the lyophilization, of the residual gas which had be entrapped in the ginseng tissue upon the freezing step.

The resultant ginseng softened by the heating step according to the method of the invention has a hardness as defined hereinbefore which is in a range of 2.5 kg to 12 kg. If the crude ginseng has been softened insufficiently to such an extent that its hardness is higher than 12 kg, the cracks will be produced in the ginseng upon the lyophilization to an extent proportional to the hardness which is shown by the softened ginseng.

As the gas which may be filled into the pressurizing vessel in the step of freezing the softened ginseng under pressure, gaseous nitrogen or air is suitable, although any inert and non-toxic gas may be used for this purpose. A rather toxic gas such as carbon monoxide is not preferred due to its difficulty to handle, while a gas having a peculiar odor such as non-purified methane is not favorable since even a trace of the odor as adsorbed by the ginseng will damage the characteristic flavor of the latter. If gaseous carbon dioxide is used as the pressurizing gas, the dried product finally obtained will disadvantageously get a trunk root diameter which is less by aprox. 22~25% than the initial diameter of the crude ginseng trunk root, indicating that a considerable shriveling of the trunk root occurs to impart an unfavorable figure to the lyophilized ginseng. Similarly, an exessive shriveling of the trunk root takes place when the softening treatment is immediately followed by the lyophilization as described later.

If the freezing step within the closed vessel is carried out in the pressurizing gas under a gas pressure which is super-atmospheric but lower than the value of 20 kg/cm$^2$, then the extent of the trunk shriveling which will occur upon the lyophilization is greater with decrease in the gas pressure employed. Particularly with a gas pressure below 10 kg/cm$^2$, the trunk shriveling upon the lyophilization will take place to the same extent as that is observed when the freezing step is effected merely under atmospheric pressure. With a gas pressure of not less than 20 kg/cm$^2$, on the other hand, the effect of minimizing the shriveling of the ginseng trunk is not always enhanced in proportion to the elevation of the gas pressure. It is thus inexpedient to elevate excessively the gas pressure by the economic reason of energy saving. Accordingly, the freezing step is preferably effected under a gas pressure between 20 kg/cm$^2$ and about 70 kg/cm$^2$.

After the freezing, the gas pressure is released and the frozen ginseng removed from the vessel and then introduced into an ordinary lyophilizing device, where the frozen ginseng is subsequently lyophilized under reduced pressure in a conventional manner to give a dried ginseng product. The latter thus obtained wholly retains the shape and color tone inherent to the original crude ginseng and has its branch and fibrous roots put together coherently to its trunk root; and it can easily be charged, together with a volume of aqueous ethanol for dipping, into a transparent bottle or container having an inlet which is of the diameter somewhat wider than the trunk root of the dried ginseng. In the alcoholic dipping solution, the conherently arranged branch and fibrous roots of the dried ginseng will absorb the aqueous ethanol and swell in all directions to restore the shape and color tone which are not distinct from those of crude ginseng and which are highly worthy of being appreciated aesthetically. The dipping aqueous ethanol then permeates into the dried ginseng so rapidly that the pharmacologically active ingredients can be extracted therefrom into the ethanol in nearly one week to give a useful alcoholic medicinal beverage or exilir containing a satisfactory amount of said active ingredients.

In the case where the crude ginseng is softened likewise in the heating step of the method of this invention as already stated and then directly lyophilized under reduced pressure in a usual way with omission of the aforesaid freezing step under pressure of the present method; and also in the case where the crude ginseng is likewise softened, then frozen in an inert gas under pressure, degassed, defrozen once under the atmospheric pressure and finally lyophilized under reduced pressure in a usual way, the drying rate of the ginseng upon the lyophilization process is of the same order as that obtained in the method of this invention which is comprising the steps of softening, freezing under pressure and lyophilization. In the two cases just mentioned above, however, the trunk root of the resultant dried ginseng can have a less diameter reduced by 11~22% than the initial diameter, with involving a noticeable shriveling in size and an unpleasant shape with deep wrinkles formed in the outside of the trunk root, as is observed in the case when the above-mentioned prior method including the step of forming elongate apertures in the trunk was conducted by means of the needles. Therefore, the dried ginseng as obtained in the above cases not according to this invention show the above drawbacks and are less worthy of aesthetic appreciation.

In a further embodiment of this invention, the steps of the freezing under pressure, the release of pressure by degassing and the subsequent lyophilization may be carried out successively within the one and same installation in order to shorten the time required for these steps and simplify the whole apparatus required. In this embodiment, however, the lyophilization device employed must be a modified and expensive, pressure-resistant one in which the materials of the cold trap and cooling pipes provided therein must be thicker and more pressure-resistant and be of a considerably reduced heat-conductivity and in which the sealing parts of the device must tolerate both the high pressure of the freezing step and the low pressure of the lyophilization step. It is therefore rather much more efficient, practical and profitable to employ a pressure-resistant vessel in the freezing step and separately a conventional lyophilization device in the lyophilization step of the present method as indicated hereinbefore.

This invention is further illustrated but not limited by the following Examples.

EXAMPLE 1

A cleaned crude ginseng (root of crude Panax ginseng weighing 128.4 g and with a trunk root diameter of 35.0 mm) was placed in a bag made of a polyethylene film, which was heat-sealed, heated by subjecting to the irradiation with microwave for 60 seconds by means of a domestic microwave oven (2450 MHz, 240 Watt) and then allowed to stand therein without the microwave processing. The microwave processing was again effected for one minute, after which the ginseng was allowed to stand and again heated by processing with microwaves for further one minute. The ginseng was then allowed to cool to room temperature.

The bag-packed crude ginseng reached a maximum temperature of 99.5° C. in the microwave processing operations, during which it was maintained at a temperature in the range from 60° to 99.5° C. The microwave processing operations has softened the crude ginseng and reduced its hardness (as defined herein) from original 24 kg to 2.5 kg.

The softened ginseng was removed from the polyethylene bag, and the branch roots and fibre-like roots extending from the trunk root were put together coherently in the direction along the latter. The ginseng so arranged coherently was placed in a pressure-resistant closed vessel, into which gaseous nitrogen was passed to an internal gas pressure of 30 kg/cm². The closed vessel including the softened ginseng was then transferred into a refrigerator at −15° C. where the ginseng was frozen and kept therein at −15° C. for 12 hours.

Subsequently, said vessel was released by degassing to atmospheric pressure, and the frozen ginseng war removed from the vessel and introduced into a lyophilization device of conventional tray-type, where the ginseng was placed on the tray to be lyophilized over 50 hours under the following conditions: Reduced pressure was 0.05 torr; Temperature of the cold trap was −50° C.; Tray temperature at the beginning of drying was −25° C., and was set to raise slowly to 50° C. in 16 hours. There was thus obtained 32.1 g of a dried ginseng having a trunk root diameter of 33.5 mm.

The dried ginseng obtained in the above way had no substantial shriveling in its trunk portion and retained the miscellaneous shape and color tone inherent to the crude ginseng. This ginseng was dipped in 30% aqueous ethanol drinkable as spirits to give a ginseng drug which had restored the original figure of the crude ginseng and was highly worthy of aesthetic appreciation. By the dipping of the dried ginseng for one week, the aqueous ethanol became a medicinal beverage which contained satisfactory amounts of the pharmacologically active ingredients extracted from the dried ginseng.

EXAMPLE 2

By way of comparison, a cleaned crude ginseng of the same species weighing 121.2 g and of 35.0 mm in the trunk root diameter as described in Example 1 was directly placed in a pressure-resistant vessel without effecting the softening thermal treatment of the Example 1. Gaseous nitrogen was passed into the vessel to an internal gas pressure of 30 kg/cm², immediately followed by freezing at −15° C. over 12 hours and the vessel was then degassed to atmospheric pressure. The frozen ginseng was lyophilized over 50 hours under reduced pressure in the same conditions as in Example 1 to give 34.2 g of a dried ginseng. This product had a trunk root diameter of 33.0 mm and involved little substantial shriveling in the trunk portion. However, deep cracks were observed in the trunk root and also in relatively thicker branch roots of the dried ginseng, which was therefore far less worthy of the aesthetic appreciation.

EXAMPLE 3

A cleaned crude ginseng weighing 83.7 g and having a trunk root diameter of 32.0 mm was placed in a bag of polyethylene film, which was then heat-sealed and subjected to the softening thermal treatment with microwaves in the same way as in Example 1. The heating step included the successive operations of microwave processing for 35 seconds, free standing for 30 seconds, further microwave processing for 40 seconds, free standing for 90 seconds and final microwave processing for 30 seconds, after which the ginseng was cooled to room temperature. The crude ginseng reached a maximum temperature of 100° C. by the microwave heating operations, during which it was maintained at a temperature in the range from 60° to 100° C. The heating operations had softened the crude ginseng whose hardness had reduced from 23.5 kg to 4.5 kg as defined herein.

The softened ginseng was removed from the polyethylene bag and the spreading branch roots and fibrous roots were put together coherently along the trunk root. The ginseng so coherently arranged was placed in a pressure-resistant closed vessel, into which compressed air was passed to an internal gas pressure of 20 kg/cm². The vessel including the ginseng was then transferred into a refrigerator at −15° C. where the ginseng was frozen at −15° C. over 12 hours.

Subsequently, said vessel was released by degassing to atmospheric pressure and the frozen ginseng was removed from the vessel and subjected to the lyophilization under the same conditions as described in Example 1. There was thus obtained 24.2 g of a dried ginseng product having a trunk root diameter of 30.0 mm.

The dried ginseng obtained in the above way had no substantial shriveling in its trunk portion and retained the original miscellaneous shape and color tone inherent to crude ginseng. This ginseng was dipped in 20% aqueous ethanol to give a ginseng for drugs which had restored its original shape and which was highly worth of appreciation. By the dipping of the dried ginseng for one week, the aqueous ethanol became a medical beverage containing satisfactory amounts of the pharmacologically active ingredients extracted from the ginseng.

EXAMPLE 4

This Example is also given by way of comparison. A cleaned curde ginseng weighing 120.6 g and with a trunk root diameter of 30.2 mm was used as raw material. Eleven fine metal needles of 1.5 mm diameter were inserted into the trunk root portion at the crotches thereof upwardly to the central axis of the curde ginseng to form therein the elongate apertures, immediately followed by freezing for 12 hours in a refrigerator at −15° C. The pierced and frozen ginseng was then lyophilized over 50 hours under the same conditions as in Example 1 to give 38.4 g of a dried ginseng having a trunk root diameter of 25.0 mm.

The dried ginseng thus obtained was considerably shriveled in the part of the trunk root whose diameter was 17% less than the initial diameter of that of the crude ginseng, and deep wrinkles were formed lengthwise over the outer surfaces of the trunk root portion and were not eliminated to restore the original smooth state upon dipping of the dried ginseng in 30% aqueous ethanol. Therefore, the dried ginseng product was quite inferior in shape to the crude ginseng and was far less worthy of aesthetic appreciation.

EXAMPLE 5

A cleaned crude ginseng weighing 87.5 g and having a trunk root diameter of 32.5 mm was placed in an aluminum container which was then sealed. The sealed container was heated in boiled water for ten minutes and then allowed to stand at room temperature for two minutes. This operation was repeated twice more. The crude ginseng reached a maximum temperature of 89° C. by the heating operations, which resulted in softening of the crude ginseng whose hardness had reduced from original 23.5 kg to 4.0 kg as defined herein.

The softened ginseng was removed from the aluminum container and the spreading branch roots and fibrous roots were put together coherently in the direction along the trunk root of ginseng. The ginseng so arranged coherently was placed in a pressure-resistant closed vessel, into which gaseous nitrogen was filled to an internal gas pressure of 30 kg/cm$^2$. The vessel including the ginseng was then transferred into a refrigerator at $-15°$ C. where the ginseng was frozen at $-15°$ C. over 12 hours.

Subsequently, said vessel was degassed to atmospheric pressure and the frozen ginseng was removed from the vessel and subjected to the lyophilization over 50 hours under the same conditions as in Example 1. There was thus obtained 25.0 g of a dried ginseng having a trunk root diameter of 30.5 mm.

The dried ginseng obtained in the above way had no substantial shriveling in its trunk root portion and retained the original shape and color tone inherent to the crude ginseng. This ginseng was dipped in 40% aqueous ethanol to give a ginseng product which restored the original shape and was well fit for appreciation. By the dipping of the dried ginseng for one week, the aqueous ethanol became a medical beverage which contained satisfactory amounts of the pharmacologically active ingredients extracted from the dried ginseng.

What is claimed is:

1. A method for dehydrating the raw root of a ginseng plant, which comprises the consecutive steps of:
    (a) heating the raw ginseng root which has been packed in a sealed bag or container, at a temperature of 60°–100° C. until the tissue of the ginseng root has been softened to a hardness of from half to one tenth of the original hardness of the raw ginseng root as measured by a penetrometer,
    (b) freezing the ginseng root so softened and then unpacked, in an inert gas which is under a gas pressure of 20–70 kg/cm$^2$, and
    (c) freeze-drying the pressure-frozen ginseng root in vacuo.

2. A method according to claim 1 in which the heating step is carried out by heating the packed ginseng with hot water, hot air or steam.

3. A method according to claim 1 in which the heating step is carried out by heating the packed ginseng by irradiating with microwaves.

4. A method according to claim 1 in which the heating step is continued until the raw ginseng root is softened to a reduced hardness, as defined herein, of not more than 12 kg.

5. A method according to claim 1 in which the inert gas is gaseous nitrogen or air.

* * * * *